US010555703B2

(12) United States Patent
Stapelfeldt

(10) Patent No.: US 10,555,703 B2
(45) Date of Patent: Feb. 11, 2020

(54) MONITORING OXYGEN UPTAKE OF A PATIENT UNDER ANESTHESIA

(71) Applicant: Wolf H. Stapelfeldt, Ballwin, MO (US)

(72) Inventor: Wolf H. Stapelfeldt, Ballwin, MO (US)

(73) Assignee: Wolf H. Stapelfeldt, Ballwin, MO (US)

( * ) Notice: Subject to any disclaimer, the term of this patent is extended or adjusted under 35 U.S.C. 154(b) by 324 days.

(21) Appl. No.: 15/453,700

(22) Filed: Mar. 8, 2017

(65) Prior Publication Data
US 2017/0258408 A1 Sep. 14, 2017

Related U.S. Application Data

(60) Provisional application No. 62/305,178, filed on Mar. 8, 2016.

(51) Int. Cl.
A61M 16/10 (2006.01)
A61B 5/00 (2006.01)
(Continued)

(52) U.S. Cl.
CPC .......... *A61B 5/7275* (2013.01); *A61B 5/0205* (2013.01); *A61B 5/4839* (2013.01);
(Continued)

(58) Field of Classification Search
CPC ..... A61B 5/7275; A61B 5/083; A61B 5/0833; A61B 5/0205; A61M 2230/30;
(Continued)

(56) References Cited

U.S. PATENT DOCUMENTS

2002/0068877 A1* 6/2002 Abramovitch ........... A61B 5/01
600/549
2006/0201507 A1 9/2006 Breen
(Continued)

OTHER PUBLICATIONS

Sessler, Daniel I., et al. "Hospital stay and mortality are increased in patients having a "triple low" . . . " Anesthesiology: The Journal of the American Society of Anesthesiologists 116.6 (2012): 1195-1203 (Year: 2012).*

(Continued)

*Primary Examiner* — Niketa I Patel
*Assistant Examiner* — Nathan A Baldwin
(74) *Attorney, Agent, or Firm* — Tarolli, Sundheim, Covell & Tummino LLP

(57) ABSTRACT

Systems and method are provided for monitoring a patient during surgery. An anesthetic machine includes a ventilator configured to provide breathable gas to a patient, an oxygen concentration sensor configured to monitor the concentration of oxygen in gas inhaled and exhaled by the patient, and a respiratory monitor configured to monitor a respiratory rate and a tidal volume of the patient. An uptake rate estimator is configured to estimate a pulmonary oxygen uptake rate (ViO2) for the patient from the concentration of oxygen in gas inhaled and exhaled by the patient and a minute volume of the patient. A risk score calculator is configured to determine a risk score for the patient at each interval as a function of the estimated ViO2 value. An output device is configured to provide the determined risk score to a human operator.

15 Claims, 2 Drawing Sheets

(51) Int. Cl.
*A61B 5/0205* (2006.01)
*A61M 16/01* (2006.01)
*A61B 5/08* (2006.01)
*A61B 5/083* (2006.01)
*A61B 5/091* (2006.01)

(52) U.S. Cl.
CPC ............ *A61B 5/742* (2013.01); *A61B 5/7405* (2013.01); *A61B 5/746* (2013.01); *A61B 5/7455* (2013.01); *A61M 16/01* (2013.01); *A61M 16/1005* (2014.02); *A61B 5/0816* (2013.01); *A61B 5/0833* (2013.01); *A61B 5/091* (2013.01); *A61M 2016/1025* (2013.01); *A61M 2230/30* (2013.01); *A61M 2230/42* (2013.01); *A61M 2230/435* (2013.01)

(58) Field of Classification Search
CPC .......... A61M 2230/40; A61M 2230/42; A61M 2230/43; A61M 2230/432435; A61M 2230/437
See application file for complete search history.

(56) References Cited

U.S. PATENT DOCUMENTS

| | | | |
|---|---|---|---|
| 2007/0125377 A1 | 6/2007 | Heinonen et al. | |
| 2008/0194489 A1* | 8/2008 | Khan | A61K 38/06 514/1.1 |
| 2011/0082380 A1* | 4/2011 | Breen | A61M 16/12 600/532 |
| 2011/0087117 A1 | 4/2011 | Tremper et al. | |
| 2012/0053433 A1 | 3/2012 | Chamoun et al. | |
| 2012/0245439 A1* | 9/2012 | Andre | A61B 5/0205 600/310 |
| 2014/0107504 A1* | 4/2014 | Stapelfeldt | A61B 5/4821 600/485 |
| 2016/0058613 A1* | 3/2016 | Palazzolo | A61N 2/006 607/105 |

OTHER PUBLICATIONS

International Application No. PCT/US17/21425, Filed Mar. 8, 2017, Applicant: Stapelfeldt, Wolf, International Search Report and Written Opinion, Authorized Officer: Lee W. Young, dated May 25, 2017, 7 pgs.

* cited by examiner

MONITORING OXYGEN UPTAKE OF A PATIENT UNDER ANESTHESIA

RELATED APPLICATIONS

This application claims priority from U.S. Patent Application Ser. No. 62/305,178, filed 8 Mar. 2016, which is incorporated herein in its entirety.

TECHNICAL FIELD

This invention relates to medical systems, and more particularly, monitoring oxygen uptake of a patient under anesthesia.

BACKGROUND

Major advances in anesthetic care over recent decades have led to a substantial reduction in intraoperative mortality. In contrast, longer term outcomes following surgery have remained less favorable, showing 30-day mortality rates upwards of 1-2% in the U.S. and even greater percentages worldwide. While intensive care unit care is being credited with having contributed to overall improved postoperative survival, the identification of those patients most likely to benefit from more intensive follow-up care (due to particularly increased risk beyond that of a higher ASA classification) has remained challenging.

SUMMARY OF THE INVENTION

In accordance with an aspect of the present invention, a system is provided for monitoring a patient during surgery. An anesthetic machine includes a ventilator configured to provide breathable gas to a patient, an oxygen concentration sensor configured to monitor the concentration of oxygen in gas inhaled and exhaled by the patient, and a respiratory monitor configured to monitor a respiratory rate and a tidal volume of the patient. A non-transitory computer readable medium is operatively connected to an associated processor and stores executable instructions for determining a risk score for a patient. The executable instructions include an uptake rate estimator configured to estimate a pulmonary oxygen uptake rate (ViO2) for the patient from the concentration of oxygen in gas inhaled and exhaled by the patient and a minute volume of the patient and a risk score calculator configured to determine a risk score for the patient at each interval as a function of the estimated ViO2 value. An output device is operatively connected to the non-transitory computer readable medium and the processor and configured to provide the determined risk score to a human operator.

In accordance with another aspect of the present invention, a method is provided for assessing a patient's risk for postoperative complications and for assigning a patient to post-surgical care. Each of a respiratory rate, a tidal volume, a fraction of inspired oxygen, and a fraction of expired oxygen are monitored for a patient under anesthesia. A pulmonary oxygen uptake rate (ViO2) is estimated at periodic intervals for the patient from the monitored respiratory rate, tidal volume, fraction of inspired oxygen, and fraction of expired oxygen to produce a time series of ViO2 values. A representative ViO2 value is determined from the time series of ViO2 values. A risk score for the patient is determined as a function of the representative ViO2 value. The patient is assigned to a first post-surgical care option if the risk score meets a threshold value and to a second post-surgical care option if the risk score fails to meet the threshold value.

In accordance with yet another aspect of the present invention, a method is provided for monitoring a patient during surgery. Each of a respiratory rate, a tidal volume, a fraction of inspired oxygen, and a fraction of expired oxygen is monitored for a patient under anesthesia. A pulmonary oxygen uptake rate (ViO2) for the patient is estimated at periodic intervals from the monitored respiratory rate, tidal volume, fraction of inspired oxygen, and fraction of expired oxygen. A risk score for the patient at each interval is determined as a function of the estimated ViO2 value. One of a visible alert, an audible alert, and a tactile alert is provided if the determined risk score meets a threshold value.

DETAILED DESCRIPTION

The inventor has provided systems and methods for monitoring the status of a patient during a surgical procedure and assigning the patient to post-surgical care. To this end, each of an arterial blood pressure, an inhaled anesthetic depth, and an estimated pulmonary oxygen uptake rate can be monitored and utilized to calculate a risk score. The risk score can be calculated during surgery from these factors and used to assist in decision making both during and after the surgical procedure. The inventor has found, contrary to accepted practice, that the risk of adverse outcomes for the patient actually increases with pulmonary oxygen uptake and decreases, within reasonable parameters, with the inhaled anesthetic depth. Accordingly, it is believed that the use of this risk score in surgical decision making can decrease the risk of adverse outcomes for patients.

Figure 1:
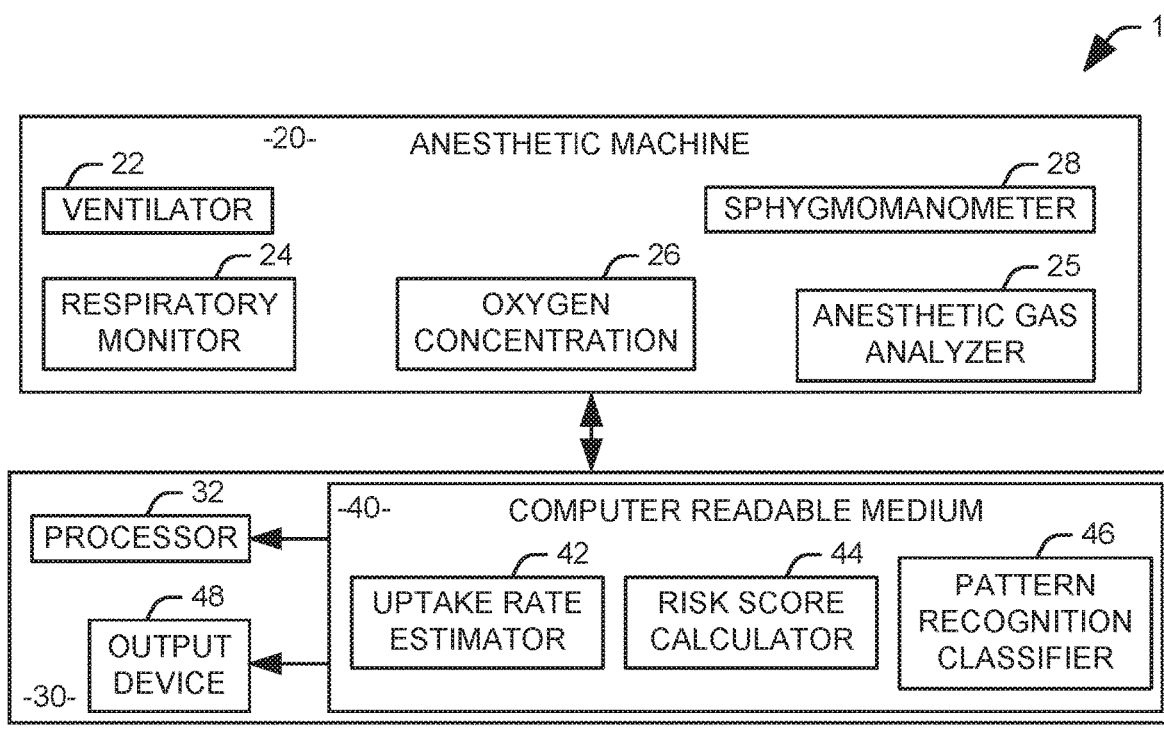
FIG. 1 illustrates one example of system for monitoring anesthesia delivered to a patient during surgery.

FIG. 1 illustrates one example of system 10 for monitoring anesthesia delivered to a patient during surgery. The system 10 includes an anesthetic machine 20 configured to deliver anesthetic to the patient to induce and maintain an anesthetized state. In the illustrated example, that includes a ventilator 22 configured to provide breathable gas to the patient. The ventilator 22 can be operatively connected to a respiratory monitor 24 configured to monitor a respiratory rate and tidal volume of the patient. The anesthetic gas analyzer 25 provides end-tidal anesthetic gas concentrations that are used to determine and track inhaled anesthetic depth of the patient from the provided gas. In the illustrated implementation, the inhaled anesthetic depth is represented as a ratio of the inhaled concentration to an age-adjusted minimum alveolar concentration (MAC) for the anesthetic, such that the inhaled anesthetic depth is expressed as multiples of the MAC. It will be appreciated, however, that an independent respiratory monitor can be used to monitor the respiratory rate and tidal volume of a patient breathing spontaneously and the inhaled anesthetic depth. An oxygen concentration sensor 26 is configured to monitor the concentration of oxygen in gas inhaled and exhaled by the patient. A sphygmomanometer 28 or invasive pressure transducer (not shown) monitors and tracks arterial blood pressure of the patient.

The data collected at the respirator monitor 24, the oxygen concentration sensor 26, the anesthetic gas analyzer 25 and the sphygmomanometer 28 can be provided to an assembly 30 for determining a risk score for the patient. The assembly 30 includes a processor 32 and a non-transitory computer readable medium 40, operatively connected to the processor 32, that stores executable instructions for determining the risk score. An uptake rate estimator 42 is configured to estimate a pulmonary oxygen uptake rate (ViO2) for the patient from the concentration of oxygen in gas inhaled and exhaled by the patient and a minute volume of the patient. It will be appreciated that the minute volume can be estimated from the measured respiratory rate and tidal volume of the patient. A risk score calculator 44 is configured to determine a risk score for the patient at each interval as a function of the estimated ViO2 value.

In one implementation, the system 10 is configured to monitor a patient during surgery to alert a user of situations that might represent an increased risk of adverse outcomes for the patient. In one example of this implementation, each of the ViO2 value, the blood pressure, and the inhaled anesthetic depth is measured or calculated from appropriate measurements every fifteen seconds, and representative values for these parameters are calculated each minute. For example, the representative value can be a measure of central tendency, such as an arithmetic mean, a geometric mean, or a median of the values. In another implementation, the representative values are weighted linear combinations of the individual values. The risk score is calculated every minute from these values. In the illustrated example, the risk score, $R_{SLU}$, is calculated from an arithmetic mean of the arterial blood pressure, $\overline{MAP}$, an arithmetic mean of the inhaled anesthetic depth, $\overline{MAC}$, measured in multiples of an age-adjusted minimum alveolar concentration, and an arithmetic mean of the estimated pulmonary oxygen uptake rate, $\overline{ViO2}$, such that:

$$R_{SLU} = \frac{\overline{ViO2}}{\overline{MAP} * \overline{MAC}} \quad \text{Eq. 1}$$

In another implementation, the system 10 includes a pattern recognition classifier 46 configured to classify a patient into one of a plurality of classes representing need for different levels of post-surgical care. In a simplified example, the classes can include a first class of patients who can be released after a recovery period on the day of the operation, a second class requiring observation overnight, a third class requiring an enhanced level of care, and a fourth class requiring intensive care. In one example of this implementation, each of the ViO2 value, the blood pressure, and the inhaled anesthetic depth is measured or calculated from appropriate measurements every fifteen seconds, and representative values for these parameters are calculated at the end of the surgery, with a risk score calculated for each interval as well as from the representative values at the end of surgery. For example, the representative value can be a measure of central tendency, such as an arithmetic mean, a geometric mean, or a median of the values. In other implementation, representative values are determined each minute of the surgery, for example, as an arithmetic mean of the measured values, with the risk score calculated each minute, and a final representative value for each parameter can be calculated as weighted linear combinations of the representative values for each minute.

Accordingly, during surgery, an operator, such as an anesthesiologist, can be made aware of the patient's risk score meeting a threshold value, for example, via an output device 48 such as a display, audible alert, or similar measure, that is operatively connected to the non-transitory computer readable medium 40 and the processor 32. In one implementation, the output device 48 is a display configured to provide the risk score to the human operator as it updates. In response to an increase in the risk score, the anesthesiologist can take measures to decrease the risk score, for example, by increasing an anesthetic gas concentration provided to the patient to increase the inhaled anesthetic depth or by choosing another means such as the additional administration of an intravenous anesthetic agent to deepen anesthetic depth and reduce oxygen consumption and uptake and/or the administration of a vasoactive agent to restore mean arterial blood pressure lowered by the anesthetic agents.

The risk score at the end of the surgery is calculated from the representative values, and the patient is classified into an appropriate post-surgical care class according to the risk score. Optionally, other features, drawn from biometric parameters of the patient or the patient's medical history, can be used in this decision, using an appropriate classification or regression model to combine the features for a final classification. In one example, these features can include one or more of an ASA classification of the patient, an emergency status of the patient (i.e., pre-scheduled vs. emergency surgery), the risk score, an age of the patient, a heart rate of the patient, and an amount (e.g., in liters) of red blood cell transfusion given to the patient.

The pattern recognition classifier 46 can utilize one or more pattern recognition algorithms, each of which analyze the calculated features or a subset of the extracted features to determine a level of post-surgical care suitable for the patient and provide this information to the output device 48. Where multiple classification algorithms are used, an arbitration element can be utilized to provide a coherent result from the plurality of classifiers. Each classifier is trained on a plurality of training samples representing the classes of interest, for example, drawn from medical records from previous surgical procedures. The training process of a given classifier will vary with its implementation, but the training generally involves a statistical aggregation of training data from the training data into one or more parameters associated with the output class. Any of a variety of optimization techniques can be utilized for the classification algorithm, including support vector machines, self-organized maps, fuzzy logic systems, data fusion processes, ensemble methods, rule based systems, or artificial neural networks.

A SVM classifier can utilize a plurality of functions, referred to as hyperplanes, to conceptually divide boundaries in the N-dimensional feature space, where each of the N dimensions represents one associated feature of the plurality of features. The boundaries define a range of feature values associated with each class. Accordingly, an output class and an associated confidence value can be determined for a given set of input features according to its position in feature space relative to the boundaries. A rule-based classifier applies a set of logical rules to the extracted features to select an output class. Generally, the rules are applied in order, with the logical result at each step influencing the analysis at later steps. A regression model can be configured to calculate a parameter representing a likelihood of post-surgical complications based on a set of predetermined weights applied to the features, with the post-surgical care determined from the calculated likelihood.

An ANN classifier comprises a plurality of nodes having a plurality of interconnections. The feature values are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier. In a binary classification, for example, classifying patients into "complication" and "no complications" classes, the final layer of nodes can include only a single node, which can be translated to a confidence value that post-surgical complications will occur.

Figure 3:
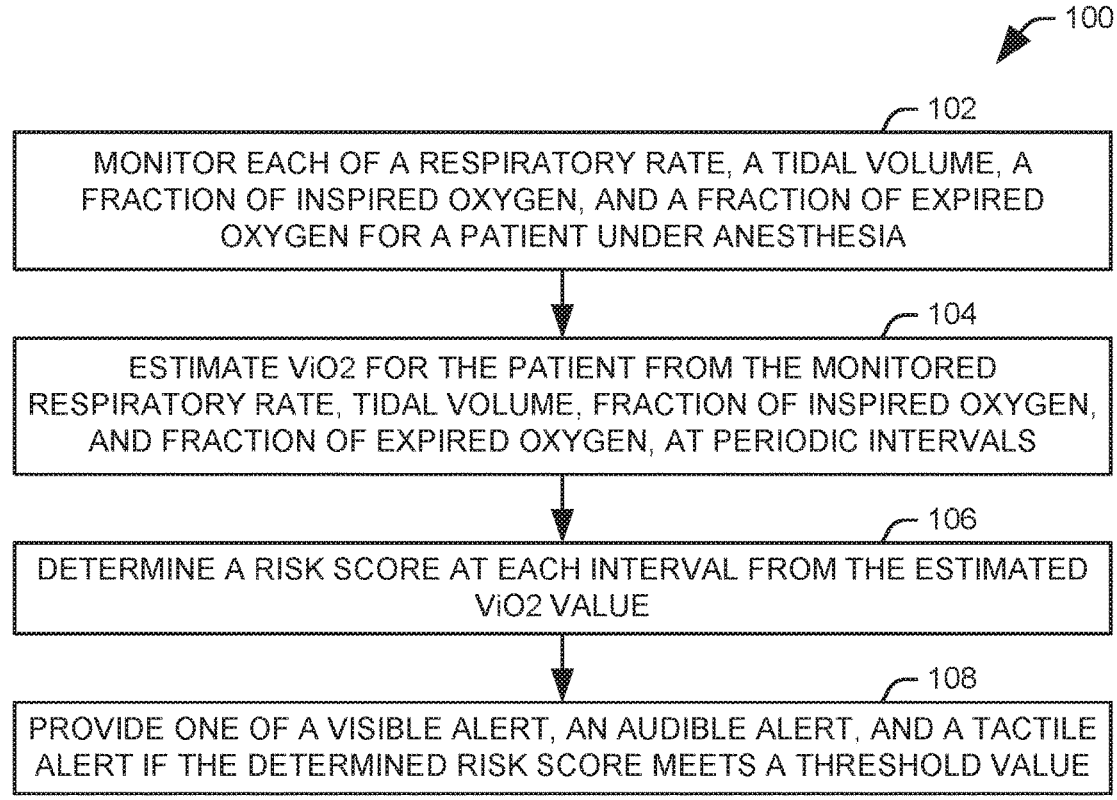
FIG. 3 illustrates a method for monitoring a patient during surgery.
Figure 2:
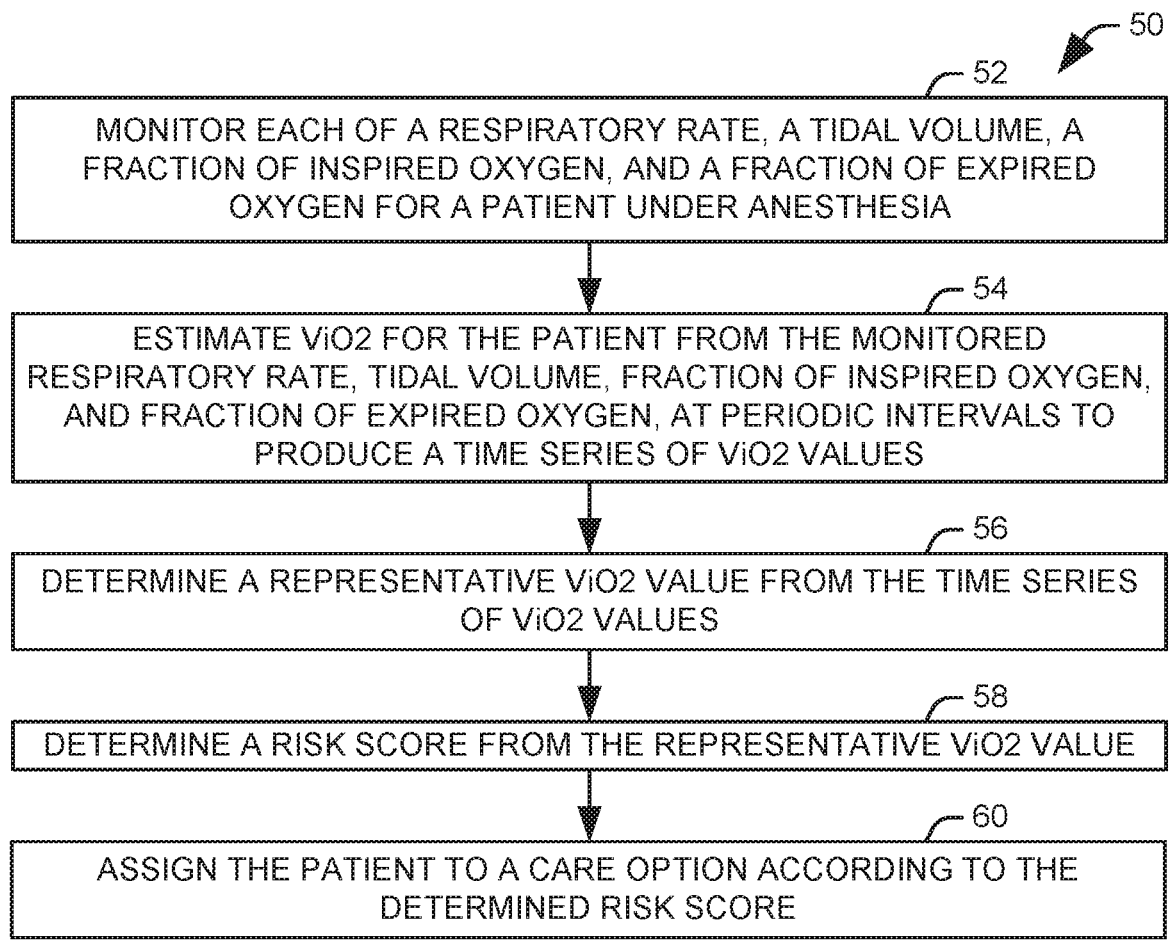
FIG. 2 illustrates a method for assessing a patient's risk for postoperative complications and for assigning a patient to post-surgical care.

In view of the foregoing structural and functional features described above in FIG. 1, example methods will be better appreciated with reference to FIGS. 2 and 3. While, for purposes of simplicity of explanation, the methods of FIGS. 2 and 3 are shown and described as executing serially, it is to be understood and appreciated that the present invention is not limited by the illustrated order, as some actions could in other examples occur in different orders and/or concurrently from that shown and described herein.

FIG. 2 illustrates a method 50 for assessing a patient's risk for postoperative complications and for assigning a patient to post-surgical care. At 52, each of a respiratory rate, a tidal volume, a fraction of inspired oxygen, and a fraction of expired oxygen are monitored for a patient under anesthesia. It will be appreciated that these values can be determined at a respirator monitor and the oxygen concentration sensor either associated with a ventilation system for the patient or independent of any ventilation system that might be used for the patient. At 54, a pulmonary oxygen uptake rate (ViO2) is estimated for the patient from the monitored respiratory rate, tidal volume, fraction of inspired oxygen, and fraction of expired oxygen, at periodic intervals to produce a time series of ViO2 values. In one implementation, the periodic interval is approximately fifteen seconds.

At 56, a representative ViO2 value is determined from the time series of ViO2 values. For example, the representative ViO2 value can be a measure of central tendency, such as a mean or median, or a weighted linear combination of the estimated values. At 58, a risk score is determined for the patient as a function of the representative ViO2 value. In one implementation, the risk score for the patient as a ratio of the representative ViO2 value to a product of a mean arterial blood pressure value for the patient and an inhaled anesthetic depth, measured in multiples of an age-adjusted MAC for the patient. At 60, the patient is assigned to a first post-surgical care option if the risk score meets a threshold value and to a second post-surgical care option if the risk score fails to meet the threshold value. For example, the patient can be assigned to an intensive care unit if the risk score exceeds the threshold and to a normal hospital floor if the risk score does not exceed the threshold. It will be appreciated, however, that in other implementations, more than two levels of care can be distinguished among or other factors may be incorporated into the assignment of the patient. For example, the risk score and other factors can be utilized as features in a classification process.

FIG. 3 illustrates a method 100 for monitoring a patient during surgery. At 102, each of a respiratory rate, a tidal volume, a fraction of inspired oxygen, and a fraction of expired oxygen are monitored for a patient under anesthesia. It will be appreciated that these values can be determined at a respirator monitor and the oxygen concentration sensor either associated with a ventilation system for the patient or independent of any ventilation system that might be used for the patient. At 104, a pulmonary oxygen uptake rate (ViO2) is estimated for the patient from the monitored respiratory rate, tidal volume, fraction of inspired oxygen, and fraction of expired oxygen, at periodic intervals to produce a time series of ViO2 values. In one implementation, a new value is estimated every minute. It will be appreciated that, in one implementation, the ViO2 values can be measured at subintervals more frequent than the time series would require, with the value at each interval determined as a mean value from its associated subintervals. For example, a value can be estimated every fifteen seconds and every four values can be averaged to produce the estimate for the time series.

At 106, a risk score is calculated for the patient at each interval as a function of the estimated ViO2 value. In one implementation, the risk score for the patient is calculated as a ratio of the representative ViO2 value to a product of a mean arterial blood pressure value for the patient and an inhaled anesthetic depth, measured in multiples of an age-adjusted MAC for the patient. At 108, one of a visible alert, an audible alert, and a tactile alert is provided if the determined risk score meets a threshold value. When an alert is received, an anesthesiologist can take appropriate measures to decrease the risk score or minimize any further increase.

Figure 4:
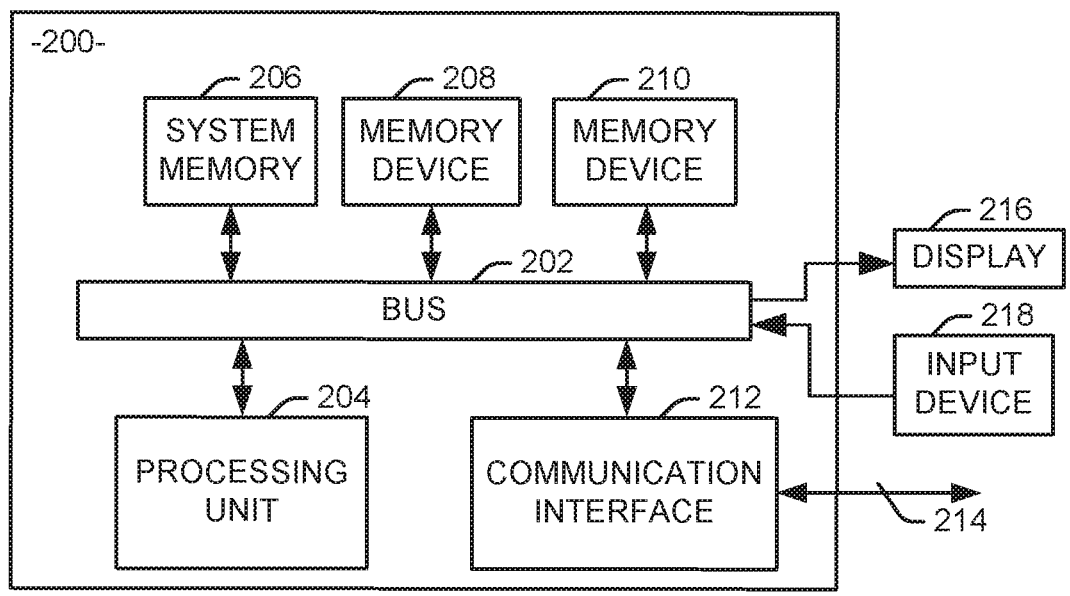
FIG. 4 is a schematic block diagram illustrating an exemplary system of hardware components capable of implementing examples of the systems and methods

FIG. 4 is a schematic block diagram illustrating an exemplary system 200 of hardware components capable of implementing examples of the systems and methods disclosed in FIGS. 1-3, such as the assembly 30 for determining a risk score for the patient illustrated in FIG. 1. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208, and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of an anesthesia monitoring system in accordance with the present invention. Computer executable logic for implementing the monitoring system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A method for assessing a patient's risk for postoperative complications and for assigning a patient to post-surgical care, comprising:
    monitoring an arterial blood pressure for the patient at a blood pressure monitor to produce a time series of arterial blood pressure values;
    determining a representative arterial blood pressure value from the time series of arterial blood pressure values;
    monitoring a respiratory rate and a tidal volume at a respiratory monitor;
    monitoring a fraction of inspired oxygen, and a fraction of expired oxygen for a patient under anesthesia at an oxygen concentration sensor;
    estimating, via stored instructions executable by a processor, a pulmonary oxygen uptake rate (ViO2) for the patient from the monitored respiratory rate, tidal volume, fraction of inspired oxygen, and fraction of expired oxygen, at periodic intervals to produce a time series of ViO2 values;
    determining, via stored instructions executable by the processor, a representative ViO2 value from the time series of ViO2 values;
    determining, via stored instructions executable by the processor, a risk score for the patient as a function of the representative ViO2 value; and
    assigning the patient to a first post-surgical care option if the risk score meets a threshold value and to a second post-surgical care option if the risk score fails to meet the threshold value, via stored instructions executable by the processor;
    wherein determining the risk score for the patient as the function of the representative ViO2 value comprises determining the risk score for the patient as a ratio of the representative ViO2 value to the representative arterial blood pressure value.

2. The method of claim 1, wherein the risk score is a linear function of the representative ViO2 value.

3. The method of claim 1, wherein the representative ViO2 value is a measure of central tendency of the time series of ViO2 values.

4. The method of claim 3, wherein the measure of central tendency of the time series of ViO2 values is a weighted average.

5. The method of claim 1, further comprising:
    monitoring an end-tidal anesthetic gas concentration of the patient at an anesthetic gas analyzer;
    determining, via stored instructions executable by the processor, an age-adjusted minimum alveolar concentration (MAC) multiple of the anesthetic from the monitored end-tidal anesthetic gas concentration to produce a time series of age adjusted MAC multiple values; and
    determining, via stored instructions executable by the processor, a representative age adjusted MAC multiple value from the time series of age adjusted MAC values;
    wherein determining the risk score for the patient as the function of the representative ViO2 value comprises determining the risk score for the patient as a ratio of the representative ViO2 value to the representative age adjusted MAC multiple value.

6. The method of claim 1, wherein determining the risk score for the patient as a function of the estimated ViO2 value, comprises determining the risk score such that the risk score increases as the estimated ViO2 value increases, and assigning the patient to the first post-surgical care option if the risk score meets the threshold value and to the second post-surgical care option if the risk score fails to meet the threshold value.

7. A method for monitoring a patient during surgery, comprising:
    monitoring a respiratory rate and a tidal volume at a respiratory monitor;
    monitoring a fraction of inspired oxygen, and a fraction of expired oxygen for a patient under anesthesia at an oxygen concentration sensor;
    estimating, via stored instructions executable by a processor, a pulmonary oxygen uptake rate (ViO2) for the patient from the monitored respiratory rate, tidal volume, fraction of inspired oxygen, and fraction of expired oxygen, at periodic intervals as a time series of estimated ViO2 values;
    monitoring an end-tidal anesthetic gas concentration of the patient at an anesthetic gas analyzer;
    determining, via stored instructions executable by the processor, an age-adjusted minimum alveolar concentration (MAC) multiple of the anesthetic from the monitored end-tidal anesthetic gas concentration to produce a time series of age adjusted MAC multiple values;
    determining, via stored instructions executable by the processor, a representative ViO2 value from the time series of ViO2 values;
    determining, via stored instructions executable by the processor, a risk score for the patient at each interval as a function of the estimated ViO2 value, wherein determining the risk score for the patient as the function of the representative ViO2 value comprises determining the risk score for the patient as a ratio of the representative ViO2 value to the representative age adjusted MAC multiple value; and providing one of a visible alert, an audible alert, and a tactile alert if the determined risk score meets a threshold value.

8. The method of claim 7, further comprising increasing an anesthetic gas concentration provided to the patient in response to the one of a visible alert, an audible alert, and a tactile alert.

9. The method of claim 7, wherein estimating a ViO2 value for the patient comprises determining a time series of estimated ViO2 values, the method further comprising:

monitoring an arterial blood pressure for the patient at a blood pressure monitor to produce a time series of arterial blood pressure values;

determining, via stored instructions executable by a processor, a representative arterial blood pressure value from the time series of arterial blood pressure values; and determining, via stored instructions executable by the processor, a representative ViO2 value from the time series of ViO2 values;

wherein determining the risk score for the patient as the function of the representative ViO2 value comprises determining the risk score for the patient as a ratio of the representative ViO2 value to the representative arterial blood pressure value.

10. A system, comprising:
a blood pressure monitor that monitors an arterial blood pressure for the patient to produce an arterial blood pressure value;
an anesthetic machine, comprising:
  a ventilator that provides breathable gas to a patient;
  an anesthetic gas analyzer that monitors an end-tidal anesthetic gas concentration of the patient; and
  an oxygen concentration sensor that monitors the concentration of oxygen in gas inhaled and exhaled by the patient;
  a respiratory monitor that monitors a respiratory rate and a tidal volume of the patient;
a non-transitory computer readable medium operatively connected to an associated processor and storing executable instructions for determining a risk score for a patient, the executable instructions comprising:
  an uptake rate estimator that estimates a pulmonary oxygen uptake rate (ViO2) for the patient at periodic intervals from the concentration of oxygen in gas inhaled and exhaled by the patient and a minute volume of the patient; and
  a risk score calculator that determines a risk score for the patient at each interval as a ratio of the estimated ViO2 value to a product of the age adjusted MAC multiple value and the arterial blood pressure value; and
an output device operatively connected to the non-transitory computer readable medium and the processor and that provides the determined risk score to a human operator.

11. The system of claim 10, further comprising a blood pressure monitor that monitors an arterial blood pressure for the patient to produce an arterial blood pressure value, the risk score calculator determining the risk score for the patient as a function of the estimated ViO2 value and the arterial blood pressure value.

12. The system of claim 10, wherein the risk score calculator determines respective time series of estimated ViO2 values, age adjusted MAC multiple values, and arterial blood pressure values across a plurality of intervals, determines a representative ViO2 value from the time series of ViO2 values, determines a representative age adjusted MAC multiple value from the time series of age adjusted MAC multiple values, determines a representative arterial blood pressure value from the time series of arterial blood pressure values, and determines an overall risk score for the patient as a ratio of the representative ViO2 value to a product of the representative age adjusted MAC multiple value and the representative arterial blood pressure value.

13. The system of claim 10, wherein the risk score calculator determines a time series of estimated ViO2 values across a plurality of intervals, determines a representative ViO2 value from the time series of ViO2 values, and determines an overall risk score for the patient from the representative ViO2 value.

14. The system of claim 13, further comprising a pattern recognition classifier that assigns the patient to one of a plurality of classes representing post-surgical care options according to a plurality of features, the plurality of features including the overall risk score.

15. The system of claim 10, wherein the output device provides one of a visible alert, an audible alert, and a tactile alert if the risk score meets a threshold value.

* * * * *